(12) United States Patent
Yen

(10) Patent No.: US 7,285,677 B1
(45) Date of Patent: Oct. 23, 2007

(54) SYSTEM AND METHOD FOR RECOVERING CTA RESIDUES AND PURIFYING/REGENERATING CATALYST

(75) Inventor: David Yen, Tao-Yuan Hsien (TW)

(73) Assignee: Mechema Chemicals International Corp., Tao-Yuan Hsien (TW)

( * ) Notice: Subject to any disclaimer, the term of this patent is extended or adjusted under 35 U.S.C. 154(b) by 0 days.

(21) Appl. No.: 11/558,976

(22) Filed: Nov. 13, 2006

(51) Int. Cl.
*C07C 51/16* (2006.01)

(52) U.S. Cl. .................. 562/414; 562/412; 562/485

(58) Field of Classification Search .......... 562/414, 562/412, 485
See application file for complete search history.

(56) References Cited

U.S. PATENT DOCUMENTS 4,786,752 A * 11/1988 Holzhauer et al. ........ 562/414
5,955,394 A * 9/1999 Kelly ....................... 502/12

* cited by examiner

*Primary Examiner*—Yvonne Eyler
*Assistant Examiner*—Sudhakar Katakam
(74) *Attorney, Agent, or Firm*—Ming Chow; Sinorica, LLC

(57) ABSTRACT

A system/method for recovering CTA (crude terephthalic acid) residues and purifying and regenerating catalyst, being used for recovering residues generated in the reaction processes of oxidation in manufacturing PTA (purified terephthalic acid) as well as purifying and regenerating the residues to form oxidized catalyst to be circulated for reusing; wherein there are mainly a CTA residue recovering system and a catalyst purifying/regenerating system. The CTA residue recovering system treats the CTA residues and collects metallic salt that is then sent to the catalyst purifying/regenerating system and is reduced by electrolyzing metal cobalt with a cobalt purifying/ regenerating system, then is passed to an oxidized catalyst producing system to produce oxidized catalyst to be circulated for use in the oxidation reaction process for manufacturing PTA.

28 Claims, 6 Drawing Sheets

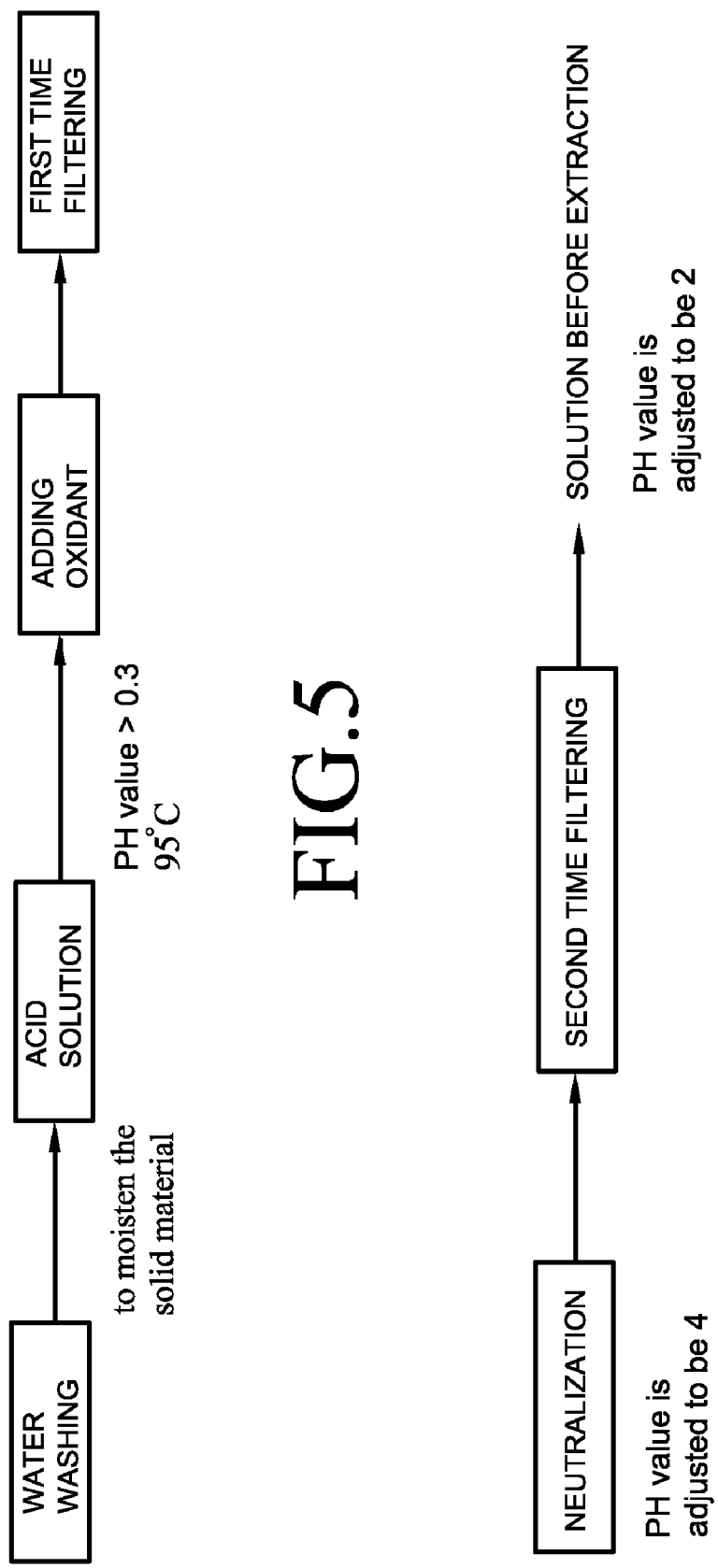

SYSTEM AND METHOD FOR RECOVERING CTA RESIDUES AND PURIFYING/REGENERATING CATALYST

BACKGROUND OF THE INVENTION

1. Field of the invention

The present invention relates to a system and a method for recovering CTA (crude terephthalic acid) residues and for purifying and regenerating catalyst, being used in the technical field of the reaction process of oxidation in manufacturing PTA (purified terephthalic acid), and especially relates to a system and a method in which the mother liquid of the CTA generated is treated to form CTA residues and is recovered to make oxidized catalysts to be circulated for reusing.

2. Description of the Prior Art

A method of producing purified terephthalic acid (PTA) uses para-xylene (PX) as raw material to produce a kind of white powder of the purity of 99.95% through the reaction process of oxidation and hydrogenation (refining). PTA is one of the main raw materials for manufacturing polyester fiber for making polyester containers (such as PET bottles), plastic for engineering and plaster.

In a process of oxidation 20 for PTA, please refer to FIG. 1, it is mainly that air is blown into a reactor for oxidation to mix with the para-xylene (PX), catalysts and acetic acids (HAc), and to proceed to oxidation of the mixed solution under the pressure of 16.5 kg/cm$^2$G and 204° C. to produce crude terephthalic acid (CTA). And in the process of oxidation 20, oxidized catalysts containing the ions of cobalt, manganese and bromine are wanted and added, and cobalt and manganese ions of two valences are used as catalysts, bromine ion is used as initiating agent. The main ingredients of oxidized catalysts used presently are compounded from three elements Co, Mn and Br, call shortly as a CMB oxidized catalyst.

And in a process of hydrogenation 30, crude terephthalic acid (CTA) is pulped and mixed, then hydrogen is added therein to react with palladium catalyst under high temperature and high pressure, 4-carboxyl benzaldehyde (4-CBA) impurity contained therein is reduced to water soluble p-toluic acid, and is produced to form PTA after centrifugation, water washing, filtering, separating and crystal drying.

Therefore, after oxidation of CTA, the process of hydrogenation 30 is required to refine the crude terephthalic acid (CTA) to form purified terephthalic acid (PTA); hence impurities in the process of manufacturing CTA shall be separated and discharged in advance, the impurities are called as CTA residues. The discharged CTA residues further are passed through a thin film evaporator system (TFE) to separate and recover the acetic acid (HAc) contained therein, then is passed through a pulping can (POT) which is added with water to lower the temperature and is discharged, the concentrations of the cobalt and manganese ions in the CTA residues obtained each is 0.1~2 wt%; the present invention aims at taking and recovering the heavy metals in the CTA residues.

Related prior art such as the U.S. Pat. No. 3,341,470 collects catalyst by the method of incineration, and U.S. Pat. No. 6,001,763 uses electric arc or electric torch of the field of electricity or plasma to produce catalysts of metallic power etc.; these are all energy consumptive manufacturing processes, and wherein the process for manufacturing terephthalic acid react under high temperatures and in acids, this makes the metallic alloys (Fe, Ni, Zn, Cr, Cu and Pb etc.) contaminated in the reaction instruments unable to be separated.

Catalyst recovering methods available presently are all chemical methods, they are recovering methods unable to separate the discharged catalysts and the impurities, such as those catalysts recovered by conventional recovering methods in the process of oxidation, this may induce accumulation of impurities during circulation. Thereby these conventional recovering methods are required to be improved.

SUMMARY OF THE INVENTION

In view of the above problems in prior arts, the present invention provides a system and a method for recovering CTA (crude terephthalic acid) residues and purifying and regenerating catalyst, being used for recovering CTA (crude terephthalic acid) residues generated in the reaction processes of oxidation in manufacturing PTA (purified terephthalic acid) as well as purifying and regenerating the residues to form oxidized catalyst to be circulated for reusing; wherein there are mainly a CTA (crude terephthalic acid) residue recovering system and a catalyst purifying/regenerating system. The CTA (crude terephthalic acid) residue recovering system treats the CTA residues and collects metallic salt that is then sent to the catalyst purifying/regenerating system, and is reduced by electrolyzing metal cobalt with a cobalt purifying/regenerating system, then is passed to an oxidized catalyst producing system to produce oxidized catalyst to be circulated for use in the oxidation reaction process for manufacturing PTA.

The system and the method for recovering CTA (crude terephthalic acid) residues provided in the present invention uses water as a medium, the organics and metallic ions in the residues of CTA are separated in the first place, then the organics and metallic ions are processed respectively with impurity removing and purifying.

The method for recovering CTA residues includes the following steps:

water washing the CTA (crude terephthalic acid) residues: the CTA residues are added with water for stirring in order to scatter the catalyst discharged from a process of oxidation of the PTA (purified terephthalic acid) into water;

first time filtering and separating: the catalyst resolved in the water is separated from solid organic material;

sedimentation: the catalyst resolved in the water is added with inorganic alkali being used as an agent for sedimentation to collect the metallic ions in the water, and the concentration of the metallic ions in the water is lowered to a level to be able of being discharged, and metallic salt is generated;

second time filtering and separating: the metallic salt is filtered and collected to be sent to a catalyst purifying and regenerating system for recovering.

The system and the method provided in the present invention can save the procedure of incineration process, this can avoid forming powered dust by incineration to make pollution; and the materials generated by the method of treatment of the present invention are carbonate or hydroxide etc., they are solid cakes being easy for collection.

The water amount for water washing in the present invention is about 5-12 times of the gross amount of the organic material depending on the ratio of the discharged material in various processes of manufacturing. The rate of recovering can be controlled to be larger than 90%.

Further, in the system and the method for purifying and regenerating catalyst provided in the present invention, and particularly in a system and a method for purifying and regenerating cobalt, a CTA (crude terephthalic acid) residue recovering system is used to recover CTA (crude terephthalic acid) residues and to produce solid metallic salt in the first place, and a PTA (purified terephthalic acid) mother liquid recovering system is used to recover PTA (purified terephthalic acid) mother liquid and to produce cobalt containing inorganic acid solution which is treated by purifying and regenerating in the manufacturing process of the present invention to get metal cobalt of high purity as well as extremely low impurity content to be provided for a subsequent oxidized catalyst producing system to reproduce oxidized catalyst, the catalyst then is circulated for use in the process of oxidation.

The method for purifying and regenerating cobalt includes the following steps: an acid solution step, a neutralization and sedimentation step, a resin treatment step, a metal extraction step and an electrolyzing step, in order to purify the metal salt and the cobalt containing inorganic acid solution and to regenerate metal cobalt.

According to the method of the present invention, the cobalt purifying/regenerating system can be provided to be applied to the manufacturing process of PTA for recovering catalyst after oxidation and for regenerating the catalyst.

The method of the present invention is applied particularly to obtain metal cobalt via the electrolyzing step, its impurities have better purity, and will not create accumulation of the impurities during circulation in manufacturing oxidized catalyst for use; its effect of recovering is better than that of a conventional chemical method for recovering catalyst.

The present invention will be apparent after reading the detailed description of the preferred embodiment thereof in reference to the accompanying drawings.

BRIEF DESCRIPTION OF THE DRAWINGS

FIG. 5 is a process flow diagram showing the step of acid solution action in the method of purifying and regenerating of catalyst of the present invention;

FIG. 6 is a process flow diagram showing the step of neutralization and sedimentation step in the method of purifying and regenerating of catalyst of the present invention;

DETAILED DESCRIPTION OF THE PREFERRED EMBODIMENT

Figure 1:
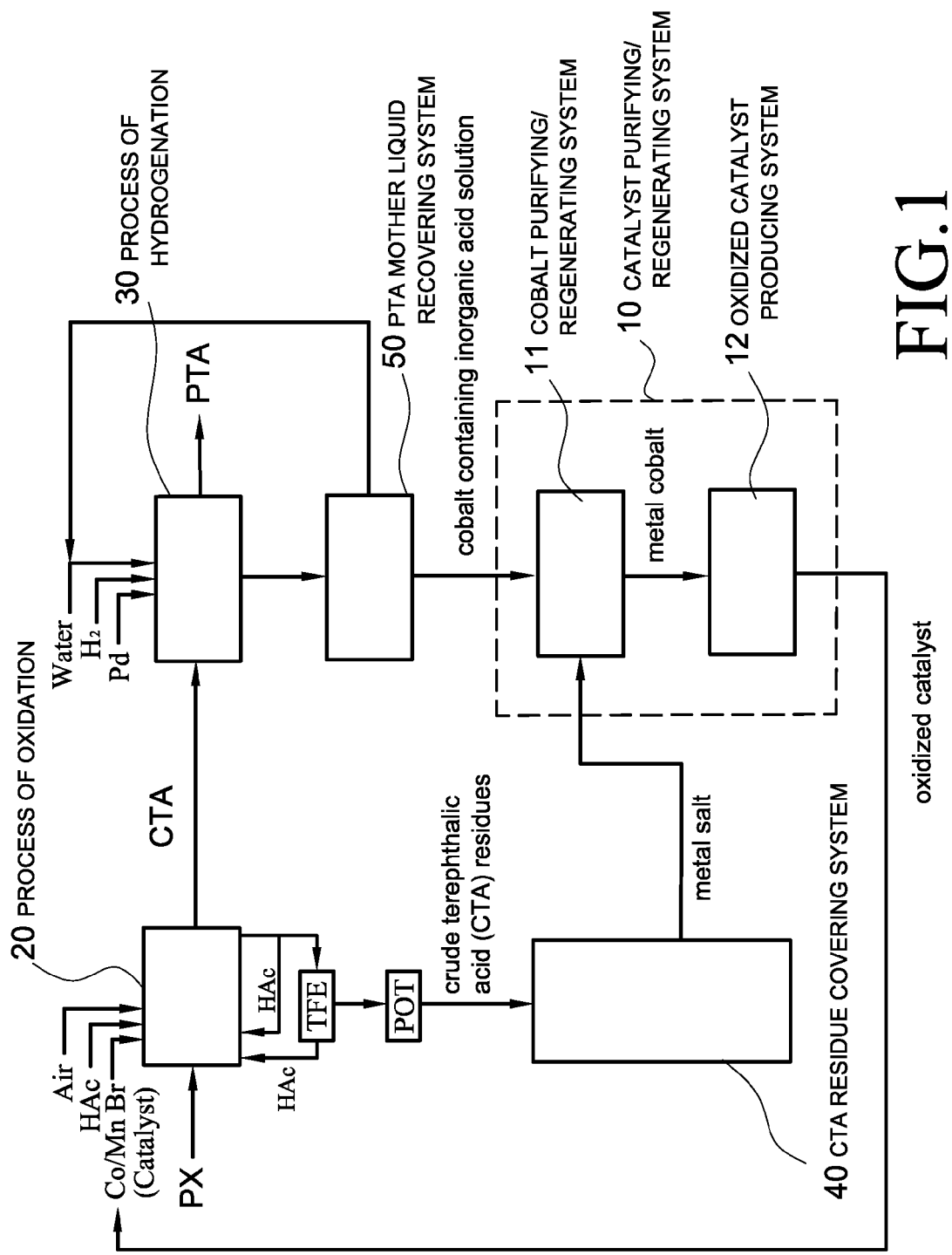
FIG. 1 is a schematic block diagram showing allocation of a system for recovering CTA (crude terephthalic acid) residues and for purifying and regenerating catalyst as well as of a system for the process of manufacturing PTA (purified terephthalic acid) of the present invention.

Referring to FIG. 1, wherein the present invention includes a CTA (crude terephthalic acid) residue recovering system 40 and a catalyst purifying/regenerating system 10, being used in the whole process of manufacturing PTA (purified terephthalic acid).

The method of producing purified terephthalic acid (PTA) uses para-xylene (PX) as raw material to produce a kind of white powder of the purity of 99.95% through a reaction process of oxidation 20 and a reaction process of hydrogenation (refining) 30.

The process of oxidation 20 mainly is to blow air into a reactor of oxidation to mix with the para-xylene (PX), catalyst and acetic acids (HAc), and to proceed to oxidation of the mixed solution under the pressure of 16.5 kg/cm$^2$ and 204° C. to produce crude terephthalic acid (CTA). Oxidized catalysts containing the ions of cobalt, manganese and bromine are wanted and added in the process of oxidation; and cobalt and manganese ions of two valences are used as catalysts, bromine ion is used as initiating agent. After the process of oxidation 20, the CTA (crude terephthalic acid) residues generated is passed through a thin film evaporator system (TFE) to separate and recover acetic acid (HAc) contained therein, then is passed through a pulping can (POT) which is added with water to lower the temperature and is discharged to obtain the residues of the crude terephthalic acid (CTA).

The residues of the crude terephthalic acid (CTA) are recovered with the crude terephthalic acid (CTA) residue recovering system 40 of the present invention to make metal salt which is sent to the catalyst purifying/regenerating system 10.

In the process of hydrogenation (refining) 30, the crude terephthalic acid (CTA) is hydrogenated to obtain PTA. The PTA mother liquid generated in the process of refining 30 is treated by a PTA mother liquid recovering system 50 and is sent to the catalyst purifying/regenerating system 10.

Figure 2:
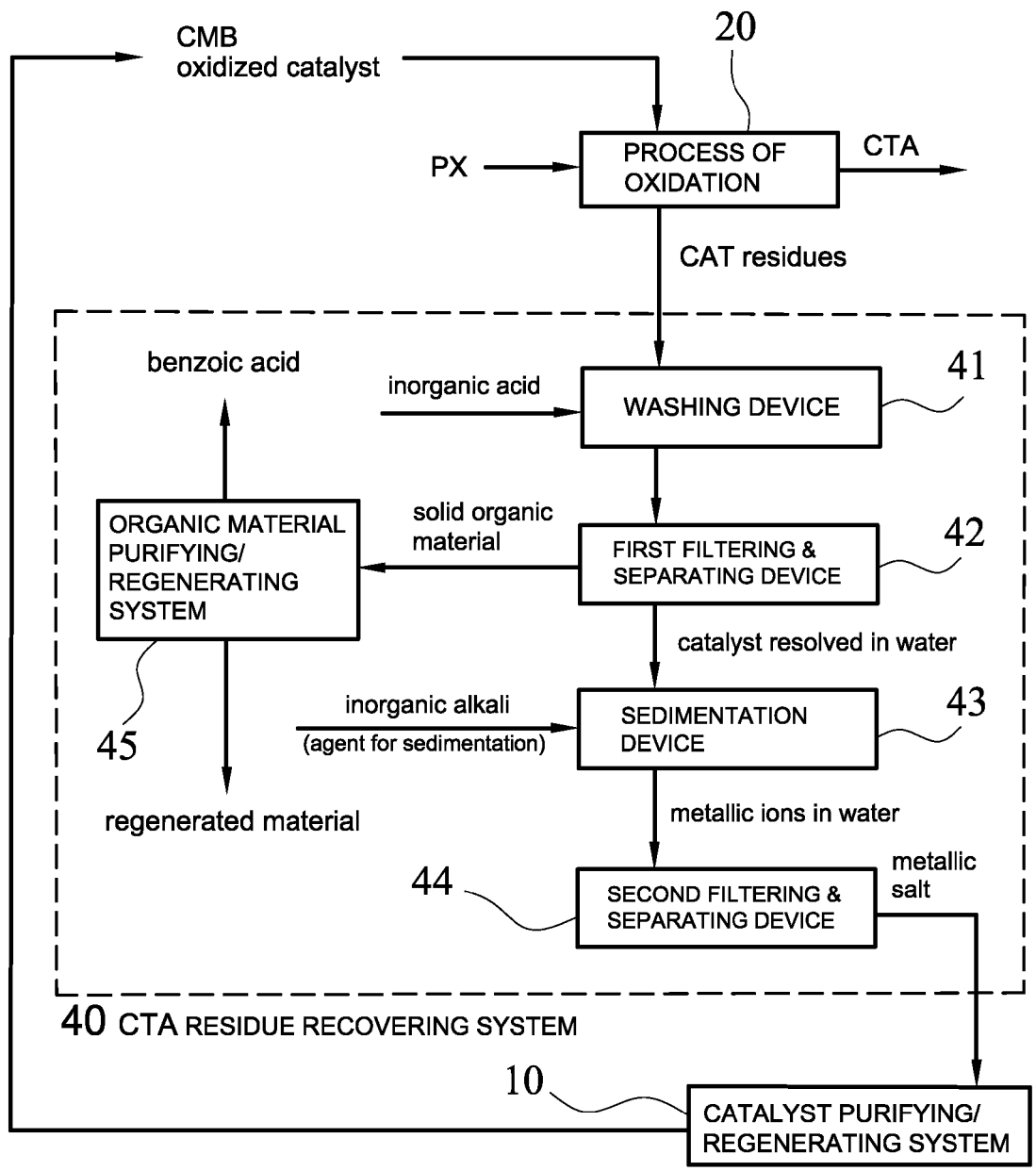
FIG. 2 is a schematic block diagram showing allocation of the CTA (crude terephthalic acid) residue recovering system of the present invention.
Figure 3:
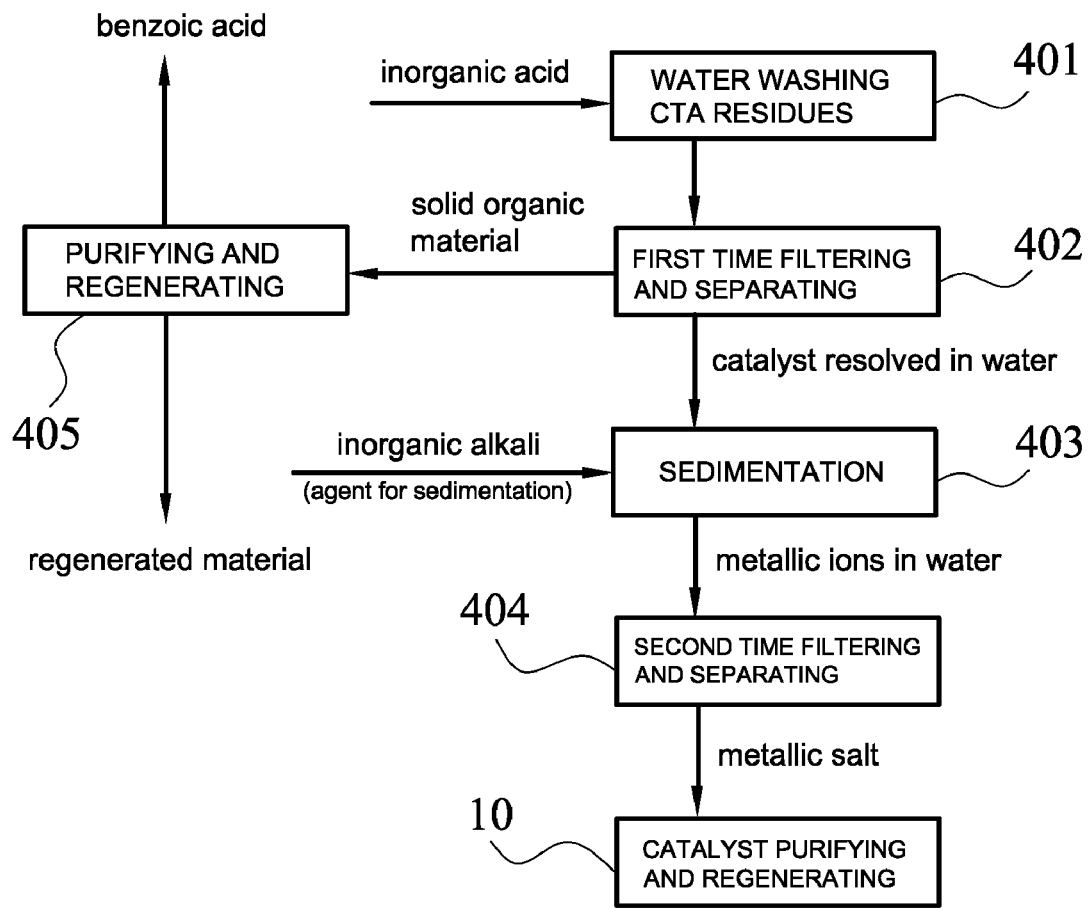
FIG. 3 is a process flow diagram showing the method of recovering CTA (crude terephthalic acid) residues of the present invention.

Further referring to FIG. 2, the system for recovering CTA (crude terephthalic acid) residues mainly includes:

a water washing device 41, the CTA residues are added with water for stirring in order to resolve the catalyst discharged from a process of oxidation of the PTA (purified terephthalic acid) into water;

a first filtering and separating device 42: the catalyst resolved in the water is separated from solid organic material;

a sedimentation device 43: wherein the catalyst resolved in the water is added with inorganic alkali being used as an agent for sedimentation to collect the metallic ions in the water, and the concentration of the metallic ions in the water is lowered to a level able of being discharged, and metallic salt is generated;

a second filtering and separating device 44: wherein the metallic salt is filtered and collected to be sent to the catalyst purifying/regenerating system 10 for recovering.

A little inorganic acid can be added to the water washing device 41 to increase the efficiency of resolution, the inorganic acid added includes but is not limited to: chlorhydric acid, hydrobromic acid or sulfuric acid.

The solid organic material separated from the first filtering and separating device 42 is sent to an organic material purifying/regenerating system 45 for recovering to generate benzoic acid and regenerated material.

The method of filtering of the first filtering and separating device 42 and the second filtering and separating device 44 includes but is not limited to: bag type filtering, plate type filtering, cross-flow filtering, centrifugation filtering, Dorr type, hydracyclone or hyperflux type filtering.

The organic material filtered and separated from the first filtering and separating device 42 includes but is not limited to: terephthalic acid, o-phtalic acid, iso-phtalic acid, benzoic acid, p-toluic acid or 4-carboxyl benzaldehyde.

The inorganic alkali added in the sedimentation device 43 includes but is not limited to: sodium hydroxide, potassium hydroxide, sodium carbonate, sodium hydrogen carbonate or ammonium hydrogen carbonate.

With the crude terephthalic acid (CTA) residue recovering system 40 of the present invention, a process flow of the method of recovering the crude terephthalic acid (CTA) residues can be obtained, the followings are the steps of the method:

water washing CTA (crude terephthalic acid) residues 401: the CTA residues 401 are added with water for stirring in order to scatter the catalyst discharged from the process of oxidation of the PTA (purified terephthalic acid) into water; adjusting PH value to about 1~1.25, preferably 2, so that the content of metal in the solid organic material can be reduced;

first time filtering and separating 402: the catalyst resolved in the water is separated from the solid organic material;

sedimentation 403: the catalyst resolved in the water is added with inorganic alkali being used as an agent for sedimentation to collect the metallic ions in the water, and the concentration of the metallic ions in the water is lowered to a level to be able of being discharged, and metallic salt is generated; and second time filtering and separating 404: the metallic salt is filtered and collected and sent to the catalyst purifying/regenerating system 10.

Wherein the solid organic material separated from the step of first time filtering and separating 402 is further processed by purifying and regenerating of organic material 405 for recovering to generate benzoic acid and regenerated material.

The crude terephthalic acid (CTA) residues recovering system and method provided in the present invention can save the procedure of incineration process, this can avoid forming powered dust by incineration to make pollution; and the materials generated by the method of treatment of the present invention are carbonate or hydroxide etc., they are solid cakes being easy for collection.

The water amount for water washing in the present invention is about 5-12 times of the gross amount of the organic material depending on the ratio of the discharged material in various processes of manufacturing. The rate of recovering can be controlled to be larger than 90%.

Figure 7:
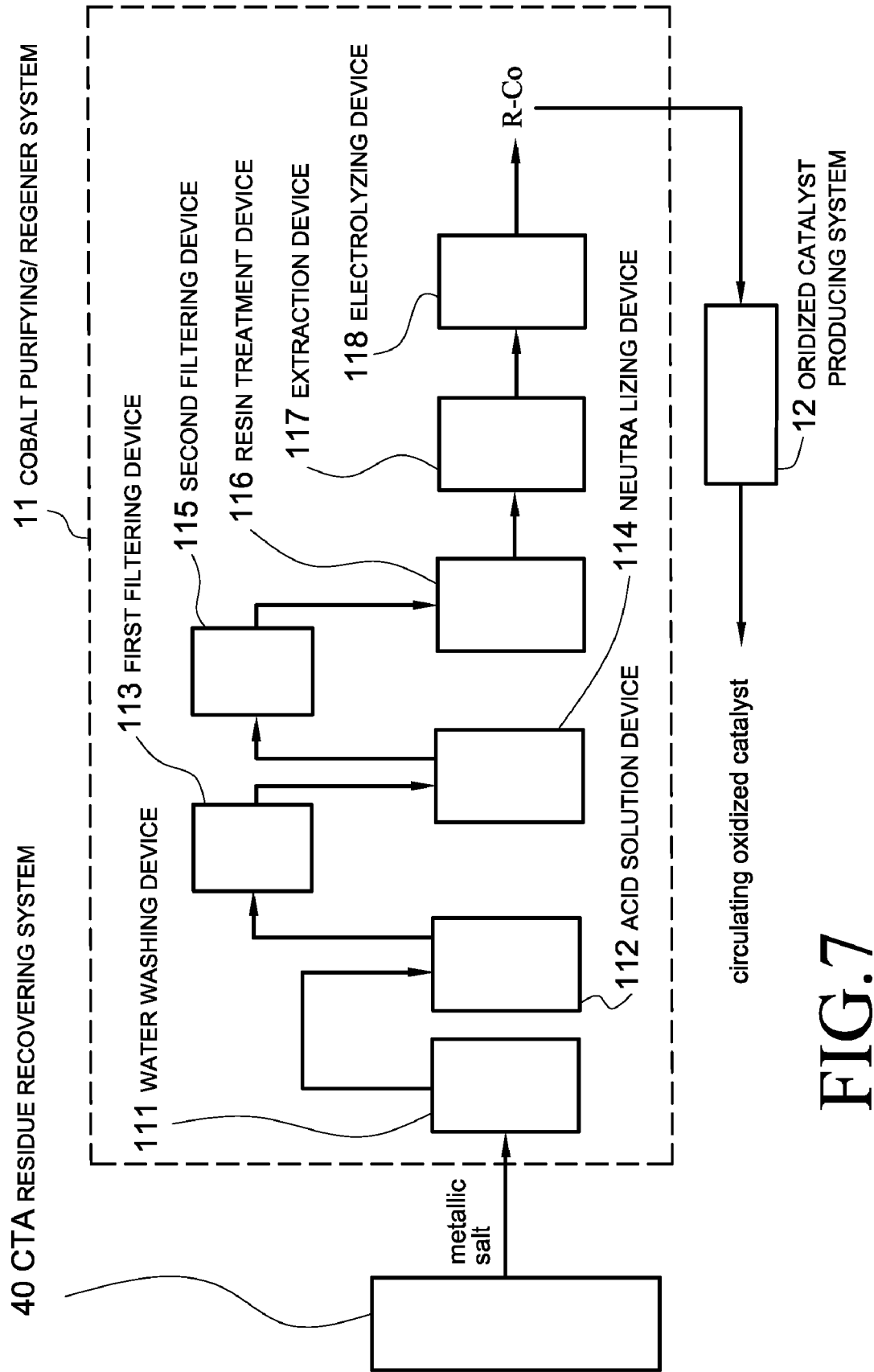
FIG. 7 is a schematic block diagram showing allocation of the system of purifying and regenerating of catalyst of the present invention.

The catalyst purifying/regenerating system 10 of the present invention, referring to FIGS. 1 and 7, mainly includes a cobalt purifying/regenerating system 11 and an oxidized catalyst producing system 12.

Figure 4:
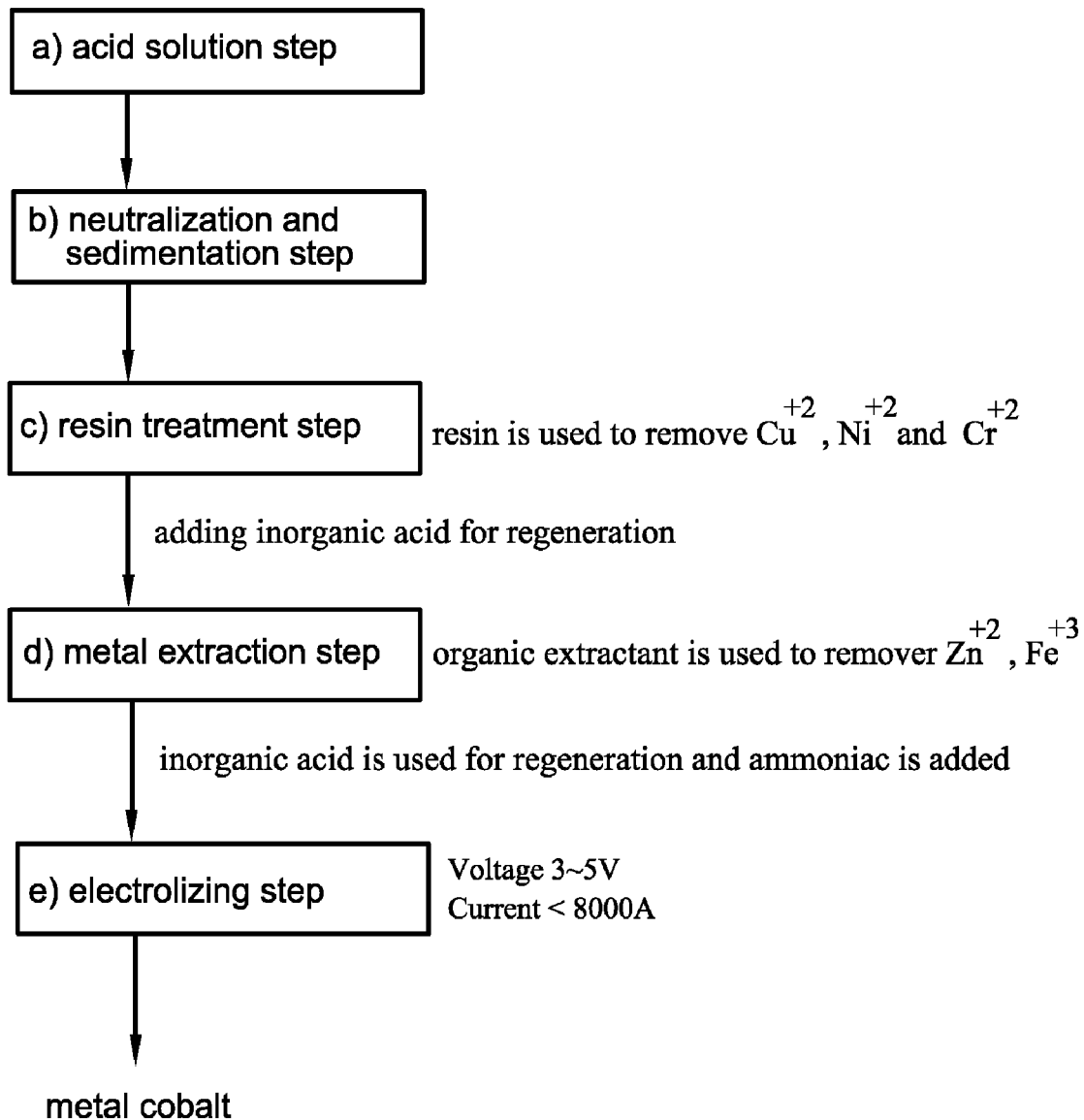
FIG. 4 is a process flow diagram showing the method of purifying and regenerating of catalyst of the present invention.

The cobalt purifying/regenerating method in the catalyst purifying/regenerating system 10, as shown in FIG. 4, includes: a) an acid solution step, b) a neutralization and sedimentation step, c) a resin treatment step, d) a metal extraction step and e) an electrolyzing step, with an object of manufacturing metal cobalt of high purity and low impurity.

Referring to FIG. 5, the acid solution step includes water washing, acid solution, adding oxidant and first time filtering.

The object of water washing mainly is to moisten the solid material (metallic salt) to help resolution of sulfuric acid, and to help washing large amount of bromine ions or organic material. Wherein the organic material includes but is not limited to: terephthalic acid, o-phtalic acid, iso-phtalic acid, benzoic acid, p-toluic acid or 4-carboxyl benzaldehyde.

The object of acid solution mainly is to resolve metal in the solid material by adding inorganic acid solution (sulfuric acid); for the sake of helping the efficiency of reaction, the controlling condition therefor is to heat up to make the temperature raised to 95° C. and to control the PH value to be below 0.3. The inorganic acid added therein, in addition to sulfuric acid, can be but is not limited to chlorhydric acid or hydrobromic acid.

The adding of oxidant mainly is to oxide $Fe^{+2}$ to form $Fe^{+3}$ for helping the neutralization step in a subsequent stage; the oxidant added includes but is not limited to potassium manganate, hydrogen peroxide, nitric acid, or introduced ozone or air.

The first time filtering uses a filtering device to separate solid material and liquid; the method of filtering includes but is not limited to bag type filtering, plate type filtering, cross-flow filtering, centrifugation filtering, Dorr type, hydracyclone or hyperflux type filtering.

Referring to FIG. 6, the neutralization and sedimentation step includes neutralization and second time filtering to form solution before extraction with an object of removing much iron (Fe) ions.

During neutralization, the controlling condition therefor is to adjust the PH value to be 4 in order to eliminate $Fe^{+3}$. The chemical reaction formula of this is:

$$Fe^{3+}+3OH^- \rightarrow Fe(OH)_3 \downarrow \text{(sediment)}.$$

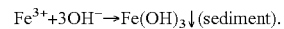

The method of second time filtering includes but is not limited to bag type filtering, plate type filtering, cross-flow filtering, centrifugation filtering, Dorr type, hydracyclone or hyperflux type filtering etc. for forming solution before extraction. The PH value of the solution before extraction shall be increased to 2-4.

In the resin treatment step, resin is used to remove copper, nickel and chromium ions; the chemical reaction formula is:

$$2R-H+Ni^{2+} \rightarrow 2R-Ni+2H+$$

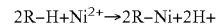

$$2R-H+Cu^{2+} \rightarrow 2R-Cu+2H+$$

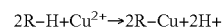

$$2R-H+Cr^{2+} \rightarrow 2R-Cr+2H+$$

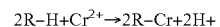

The flow rate of resin in the resin treatment step for removing copper, nickel and chromium ions is 0.5 eq/litter of resin, this can get 100% efficiency of adsorption.

Inorganic acid is used for the purpose of regenerating; the inorganic acid added is but is not limited to chlorhydric acid or hydrobromic acid or sulfuric acid.

The metal extraction step uses organic extractant to remove zinc and iron ions, the chemical reaction formula is:

$$2R-H+Zn^{2+} \rightarrow 2R-Zn+2H+$$

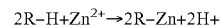

$$3R-H+Fe^{3+} \rightarrow 3R-Fe+3H+$$

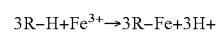

And inorganic acid can be used for regeneration; wherein inorganic acid is but is not limited to chlorhydric acid or hydrobromic acid or sulfuric acid etc.; while the extractant can be 2-ethylhexyl phosphate, butyl-dibutyl phosphonate or sec-octyl phenoxyl acid.

In the electrolyzing step, ammoniac salt is added to the amount of 1-10% before electrolyzing, and most preferably 3%, to form complex ions for preventing sedimentation of cobalt ions ($Co^{2+}$), the chemical reaction formula is:

$$Co^{+2}+6NH_3 \rightarrow Co(NH_3)_6^{+2}$$

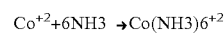

By virtue that during electrolyzing in an electrolyzing tank, the anode will acidify and shall have PH value adjusted to avoid further resolving the electrolyzed cobalt. The PH value is controlled within 4~4.2 with inorganic alkali for controlling further resolving of the electrolyzed cobalt solution. Wherein the inorganic alkali includes but is not limited to sodium hydroxide or potassium hydroxide. The voltage for electrolyzing is 3-5 V, the current is smaller than 8000 A. When the weight percentage of cobalt in electrolyzing is reduced to be smaller than 0.2%, the waste electrolyzing solution is discharged to a low cobalt content treatment area, till the concentration of cobalt become less than 10 ppm and then the waste electrolyzing solution is discharged to a waste water treatment area.

Referring to FIG. 7, the cobalt purifying/regenerating system 11 designed according to the method of the present invention is applied to the PTA manufacturing process as shown in FIG. 1 to recover catalysts for regenerating. The cobalt purifying/regenerating system 11 includes: a water washing device 111, an acid solution device 112, a first filtering device 113, a neutralization device 114, a second filtering device 115, a resin treatment device 116, an extraction device 117 and an electrolyzing device 118.

The crude terephthalic acid (CTA) residue recovering system 40 recovers catalyst to obtain solid metallic salt that enters the water washing device 111, the solid metallic salt is moistened to help resolution of sulfuric acid, and to help washing large amount of bromine ions or organic material. The moistened solid metallic salt is passed to the acid solution device 112, and inorganic acid (sulfuric acid) is added to resolve solid metallic. The solid material and liquid then are separated by treating with the first filtering device 113, the liquid obtained is sent to the neutralization device 114; the PH value of the liquid is adjusted to be 4 in order to eliminate iron ions. The liquid is passed through the second filtering device 115 to form solution before extraction. The solution before extraction is sent into the resin treatment device 116 to remove copper, nickel and chromium ions; and then is sent into the extraction device 117, organic extractant is used to remove zinc and iron ions; and then is sent into the electrolyzing device 118 to obtain metal cobalt.

The obtained metal cobalt with high purity and extremely few impurities is sent into the oxidized catalyst producing system 12 to produce oxidized catalysts which can be circulated for reusing.

The catalyst purifying/regenerating system 10 of the present invention is characterized in:

1. the neutralization step to eliminate iron ions;
2. the resin treatment step to remove copper, nickel and chromium ions;
3. the metal extraction step to remove zinc and iron ions;
4. the electrolyzing step by which metal cobalt obtained is separated from the ions of impurities of sodium (Na), potassium (K), calcium (Ca), magnesium (Mg), manganese (Mn), sulfuric acid group ($SO_4^{2-}$), ammoniac salt (NH3) etc. for manufacturing metal cobalt of high purity and low impurity, then the metal cobalt is used to produce oxidized catalyst with a CMB oxidized catalyst purifying/regenerating system, the oxidized catalyst is circulated for reusing;
5. by electrolyzing, metal cobalt with better purity and fewer impurities is regenerated;
6. In the conventional chemical method in recovering catalyst, there is no way to separate the catalyst discharged from the ion impurities, this makes accumulation of the impurities; the present invention uses a chemical method to remove impurities in the first place, and then make regeneration by electrolyzing, this is the first innovative method in the art.

The embodiment stated above is only for illustrating the present invention, and not for giving any limitation to the scope of the present invention. It will be apparent to those skilled in this art that various modifications or changes can be made to the elements of the present invention without departing from the spirit, and scope of this invention. Accordingly, all such modifications and changes also fall within the scope of the appended claims and are intended to form part of this invention.

The invention claimed is:

1. A method for recovering CTA (crude terephthalic acid) residues and purifying and regenerating catalyst, being used for recovering CTA (crude terephthalic acid) residues generated in a reaction process of oxidation in manufacturing PTA (purified terephthalic acid), said system comprises following steps:

water washing CTA (crude terephthalic acid) residues: CTA residues are added with water for stirring in order to resolve catalyst discharged from said process of oxidation of said PAT (purified terephthalic acid) into said water;

first time filtering and separating: said catalyst resolved in water is separated from solid organic material;

sedimentation: said catalyst resolved in said water is added with inorganic alkali being used as an agent for sedimentation to collect metallic ions in said water, and concentration of said metallic ions in said water is lowered to a level to be adapted for discharging, and metallic salt is generated;

second time filtering and separating: said metallic salt is filtered and collected, said catalyst then is purified and regenerated to produce oxidized catalyst from said metallic salt; and said purifying and regenerating catalyst includes steps of cobalt purifying/regenerating and oxidized catalyst producing wherein said cobalt purifying/regenerating step includes:

a) an acid solution step; to resolve solid metal by adding inorganic acid solution;

b) a neutralization and sedimentation step: to adjust pH value of said liquid to 4 to eliminate iron ions to form solution before extradition;

c) a resin treatment step: to remove copper, nickel and chromium ions from said solution before extraction;

d) a metal extraction step: to remove zinc and iron ions from said solution before extraction by extraction using organic extractant; and e) an electrolyzing step: to obtain metal cobalt by electrolyzing from liquid after extraction.

2. The method for recovering CTA (crude terephthalic acid) residues and purifying and regenerating catalyst as claimed in claim 1, wherein inorganic acid is added in during said step of CTA residue water washing to increase efficiency of resolution.

3. The method for recovering CTA (crude terephthalic acid) residues and purifying and regenerating catalyst as claimed in claim 1, wherein said solid organic material separated from said step of first time filtering and separating is further processed by organic material purifying and regenerating for recovering.

4. The method for recovering CTA (crude terephthalic acid) residues and purifying and regenerating catalyst as claimed in claim 2, wherein said inorganic acid added in a step of water washing said CTA residues is chosen from: chlorhydric acid, hydrobromic acid or sulfuric acid.

5. The method for recovering CTA (crude terephthalic acid) residues and purifying and regenerating catalyst as claimed in claim 1, wherein method of filtering for said steps of first and second time filtering and separating is chosen from: bag type filtering, plate type filtering, cross-flow filtering, centrifugation filtering, Dorr type, hydracyclone or hyperflux type filtering.

6. The method for recovering CTA (crude terephthalic acid) residues and purifying and regenerating catalyst as claimed in claim 1, wherein said organic material filtered and separated from step of first filtering and separating chosen from: terephthalic acid, o-phtalic acid, iso-phtalic acid, benzoic acid, p-toluic acid or 4-carboxyl benzaldehyde.

7. The method for recovering CTA (crude terephthalic acid) residues and purifying and regenerating catalyst as claimed in claim 1, wherein said inorganic alkali added in said step of sedimentation is chosen from: sodium hydroxide, potassium hydroxide, sodium carbonate, sodium hydrogen carbonate or ammonium hydrogen carbonate.

8. The method for recovering CTA (crude terephthalic acid) residues and purifying and regenerating catalyst as claimed in claim 1, wherein water amount for said step of water washing is about 5-12 times of a gross amount of said organic material.

9. The method for recovering CTA (crude terephthalic acid) residues and purifying and regenerating catalyst as claimed in claim 1, wherein a CTA (crude terephthalic acid) residue recovering system is used to recover CTA (crude terephthalic acid) residues and to produce solid metallic salt, and a PTA (purified terephthalic acid mother liquid recovering system is used to recover PTA (purified terephthalic acid) mother liquid and to produce cobalt containing inorganic acid solution.

10. The method for recovering CTA (crude terephthalic acid) residues and purifying and regenerating catalyst as claimed in claim 9, wherein said solution step includes:
   water washing: to moisten said metallic salt to help resolution of sulfuric acid, and to help washing large amount of bromine ions or organic material;
   acid solution: to resolve metal in solid material by adding inorganic acid solution (sulfuric acid);
   adding oxidant; to oxide $Fe^{+2}$ to form $Fe^{+3}$ for helping said neutralization step in a subsequent stage; and
   first time filtering: to separate said solid material and liquid.

11. The method for recovering CTA (crude terephthalic acid) residues and purifying and regenerating catalyst as claimed in claim 10, wherein said organic material in said water washing includes: terephthalic acid, o-phtalic acid, iso-phtalic acid, benzoic acid, p-toluic acid, or 4-carboxyl benzaldehyde.

12. The method for recovering CTA (crude terephthalic acid) residues and purifying and regenerating catalyst as claimed in claim 10, wherein controlling condition for said acid solution is to heat up and to make temperature raised to 95° C. and to control pH value to be below 0.3.

13. The method for recovering CTA (crude terephthalic acid) residues and purifying and regenerating catalyst as claimed in claim 10, wherein said inorganic acid added in said acid solution, in addition to sulfuric acid, includes chlorhydric acid or hydrobromic acid.

14. The method for recovering CTA (crude terephthalic acid) residues and purifying and regenerating catalyst as claimed in claim 10, wherein said oxidant added is chosen from: potassium manganate, hydrogen peroxide, nitric acid, or introduced ozone or air.

15. The method for recovering CTA (crude terephthalic acid) residues and purifying and regenerating catalyst as claimed in claim 10, wherein said first time filtering method is chosen from: bag type filtering, plate type filtering, cross-flow filtering, centrifugation filtering, Dorr type, hydracyclone or hyperflux type filtering.

16. The method for recovering CTA (crude terephthalic acid) residues and purifying and regenerating catalyst as claimed in claim 1, wherein said neutralization and sedimentation step includes:
   neutralization: to add $OH^-$ to $Fe^{3+}$ to get $Fe(OH)_3$ sediment, and
   second time filtering: to filter said $Fe(OH)_3$ sediment to form solution before extraction with an object of removing much iron (Fe) ions.

17. The method for recovering CTA (crude terephthalic acid) residues and purifying and regenerating catalyst as claimed in claim 16, wherein said second time filtering is chosen from: bag type filtering, plate type filtering, cross-flow filtering, centrifugation filtering, Dorr type, hydracyclone or hyperflux type filtering.

18. The method for recovering CTA (crude terephthalic acid) residues and purifying and regenerating catalyst as claimed in claim 17, wherein pH value of said solution before extraction is increased to 2.

19. The method for recovering CTA (crude terephthalic acid) residues and purifying and regenerating catalyst as claimed in claim 1, wherein flow rate of resin in said resin treatment step for removing copper, nickel and chromium ions is 0.5 eq/litter of resin that gets 100% efficiency of adsorption.

20. The method for recovering CTA (crude terephthalic acid) residues and purifying and regenerating catalyst as claimed in claim 19, in said resin treatment step, inorganic acid is used for regeneration; said inorganic acid is chosen from: chlorhydric acid or hydrobromic acid or sulfuric acid.

21. The method for recovering CTA (crude terephthalic acid) residues and purifying and regenerating catalyst as claimed in claim 19, in said metal extraction step, said extractant is 2-ethylhexyl phosphate, butyl-dibutyl phosphonate or sec-octyl phenoxyl acid.

22. The method for recovering CTA (crude terephthalic acid) residues and purifying and regenerating catalyst as claimed in claim 19, in said metal extraction step, said inorganic acid is used for regeneration, is chosen from: chlorhydric acid, hydrobromic acid or sulfuric acid.

23. The method for recovering CTA (crude terephthalic acid) residues and purifying and regenerating catalyst as claimed in claim 1, in said electrolyzing step, ammoniac salt is added to an amount of 1-10% before electrolyzing, to form complex ions for preventing sedimentation of cobalt ions ($Co^{2+}$).

24. The method for recovering CTA (crude terephthalic acid) residues and purifying and regenerating catalyst is claimed in claim 1, wherein during electrolyzing in an electrolyzing tank, pH value is controlled within 4~4.2 with inorganic alkali for controlling further resolving of electrolyzed cobalt solution.

25. The method for recovering CTA (crude terephthalic acid) residues and purifying and regenerating catalyst as claimed in claim 24, in said electrolyzing step, said inorganic alkali is chosen from: sodium hydroxide or potassium hydroxide.

26. The method for recovering CTA (crude terephthalic acid) residues and purifying and regenerating catalyst as claimed in claim 1, in said electrolyzing step, voltage for electrolyzing is 3-5 V, current is smaller than 8000 A.

27. The method for recovering CTA (crude terephthalic acid) residues and purifying and regenerating catalyst as claimed in claim 1, in said electrolyzing step, when weight percentage of cobalt in electrolyzing is reduced to be smaller than 0.2%, waste electrolyzing solution is discharged to a low cobalt content treatment area, till concentration of cobalt becomes less than 10 ppm and then said waste electrolyzing solution is discharged to a waste water treatment area.

28. The method for recovering CTA (crude terephthalic acid) residues and purifying and regenerating catalyst as claimed in claim 1, wherein metal cobalt obtained to by electrolyzing is sent into an oxidized catalyst producing system to produce oxidized catalyst to be circulated for use in said reaction process of oxidation in said manufacturing PTA (purified terephthalic acid).

* * * * *